United States Patent [19]
Loosen et al.

[11] Patent Number: 5,760,287
[45] Date of Patent: Jun. 2, 1998

[54] PROCESS FOR THE RESOLUTION OF 6-METHOXY-ALPHA-METHYL-2-NAPHTHALENEACETIC RACEMIC ACID INTO ITS ENANTIOMERS

[75] Inventors: Pierre Loosen, Tessenderlo, Belgium; Gabriele Breviglieri, Treviglio, Italy; Bruno Giagomo, Treviglio, Italy; Sergio Contrini; Cineia Assanelli, both of Treviglio, Italy

[73] Assignee: Farchemia S.R.L., Treviglio, Italy

[21] Appl. No.: 633,177

[22] Filed: Apr. 16, 1996

[30] Foreign Application Priority Data

Dec. 19, 1995 [IT] Italy .................... MI95A2668

[51] Int. Cl.$^6$ .................................... C07B 55/00
[52] U.S. Cl. .................................... 562/401; 562/466
[58] Field of Search .................... 562/401, 466

[56] References Cited

FOREIGN PATENT DOCUMENTS 46859229  1/1992  European Pat. Off. .

Primary Examiner—Paul J. Killos
Attorney, Agent, or Firm—Walter H. Schneider

[57] ABSTRACT

Naproxene ((+)-6-methoxy-α-methyl-2-naphthaleneacetic acid) is recovered from the corresponding racemic acid by treatment of the latter with N-substituted R-(−)-2-amino-1-butanols and recovery of the resulting diastereomeric salt.

3 Claims, No Drawings

PROCESS FOR THE RESOLUTION OF 6-METHOXY-ALPHA-METHYL-2-NAPHTHALENEACETIC RACEMIC ACID INTO ITS ENANTIOMERS

The present invention relates to a process for the resolution of 6-methoxy-α-methyl-2-naphthaleneacetic racemic acid (hereinafter referred to as "racemic acid", for the sake of brevity) into its enantiomers, through the separation of the diastereomeric salts of said acid with R-(−)-2-amino-1-butanol N-substituted derivatives.

(+)-6-Methoxy-α-methyl-2-naphthaleneacetic acid, i.e. Naproxene, is a well known antiphlogistic, analgesic, antipyretic medicament.

The resolution of the racemic acid into the enantiomers can be carried out according to a number of known methods, which make use of different resolution agents suitable to form diastereomeric salts (or amides). Thus, GB Patent 2,025,968 discloses the use of N-methyl glucamine; German Patent 3,025,448 describes the use of N-alkyl glucamines; EP 468,592 and U.S. Pat. No. 5,200,555 disclose the use of 2-amino-1-butanol; EP 12,854 describes the use of α-phenyl-ethylamine.

In the choice of the resolution agent for the optical resolution, the following parameters should be considered important:
a) optical purity of the resulting product
b) yield in optically active product
c) cost of the resolution agent
d) possibility of recovering and recycling easily the resolution agent
e) cost of the solvent or of the mixture of solvents used and easiness of the recovery thereof.

All of the processes suggested up to now are unsatisfactory as far as one or more of the above listed parameters are concerned.

Now it has been found, and it is the object of the present invention, that the use of R-(−)-2-amino-1-butanol N-substituted derivatives as resolution agents allows to obtain Naproxene not only in higher yield and optical purity, but highly satisfactorily also as far as parameters c), d) and e) are concerned.

The class of resolution agents according to the present invention and the use thereof as optical resolution agents have never been described in literature.

The compounds of the invention derive from R-(−)-2-amino-1-butanol by reductive alkylation and have the general formula (I)

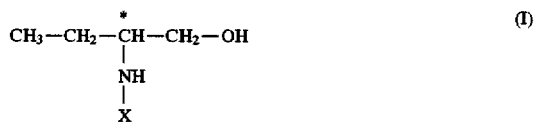

wherein the chiral atom has R configuration, whereas X is a straight or branched $C_4$–$C_{20}$ alkyl residue, or an aralkyl residue in which the alkyl portion is $C_1$–$C_4$ straight or branched, whereas the aryl portion is a phenyl, naphthyl, diphenyl, anthracene or phenanthrene ring which in its turn can carry one or more substituents, such as $C_1$–$C_4$ alkyl, $C_1$–$C_4$ alkoxy groups or halogen. Variously substituted, straight or branched aliphatic aldehydes or ketones, or variously substituted, aromatic or arylaliphatic aldehydes or ketones, can be used for the reductive alkylation of R-(−)-2-amino-1-butanol. Aldehydes are preferably used, more preferably aromatic or arylaliphatic aldehydes, examples of them being benzaldehyde, p-anisaldehyde, p-tolylaldehyde and 2-phenylpropanal.

R-(−)-2-amino-1-butanol is a side-product from the synthesis of the known antibacterial agent Ethambutol (for which the S-(+) isomer is used) and therefore is easily available and has a low cost. The resulting compounds (I) (which are a further object of the invention) are insoluble in water whereas they are easily soluble in the usual organic solvents. As it will be apparent from the following examples, such a characteristic allows an easy, high-yield recovery of the resolution agent, after the optical resolution.

The solvents used in the synthesis are easily available and have a low cost. The operative procedures also make the recovery and recycle of the solvents easy.

The yield in Naproxene is high, reaching even 80% of theoretical, as it will be seen in the examples. The optical purity of the obtained product is excellent; the enantiomeric excess (e.e.) is in fact of 99% or higher.

These characteristics make the process of the present invention very attractive from the industrial point of view compared with those reported in literature. In fact, said process is advantageous compared with the use of N-methylglucamine and 2-aminobutanol as for the easiness of recovery of the resolution agent. The cost of the latter is much lower than that of N-methylglucamine and α-phenylethylamine. The high yield in the desired isomer is exceeded by any of the prior art techniques, on the contrary, in many cases it is remarkably higher.

For the preparation of the resolution agents (I), 1 mole of aldehyde (or ketone) and 1 mole of R-(−)-2-amino-1-butanol are mixed in a suitable solvent and left to react. When the formation of the Schiff's base is completed, a suitable reduction catalyst is added, hydrogenating under atmospheric or higher pressure, depending on the selected catalyst.

At the end of the reduction, the catalyst is filtered off and the solvent is evaporated under vacuum to obtain the desired compound (I) as a residue. Suitable solvents for this purpose are alcohols, pure or in admixture with water.

Nickel Raney or metals of the VIII group, optionally on an inert carrier, for example Pd/C, can effectively be used as reduction catalysts, in a weight ratio which can range from 1% to 10% based on the aldehyde or ketone weight.

The optical resolution is carried out using the resolution agent in an amount which can range from 0.5 mol to 1 mol, preferably 0.6–0.75 moles per mole of racemic acid. The two products are mixed in a solvent (or a mixture of solvents).

Suitable solvents or mixtures are those in which the racemic acid is dissolved easily whereas the salt consisting of the D-(+)-6-methoxy-α-methyl-2-naphthaleneacetic acid and the resolution agent is sparingly soluble, for example acetone, methyl ethyl ketone, ethyl acetate, and acetone/water, toluene/methanol, toluene/ethanol mixtures. Particularly preferred are the acetone/water mixtures in volume ratios from 95/5 to 70/30 and the methyl ethyl ketone/water mixtures in the same ratios. The toluene/methanol mixture in ratios ranging from 90/10 to 70/30 can also be used successfully.

The solvent (or mixture of solvents) to racemic acid ratio can range from 2:1 to 20:1 (v/w); ratios from 4:1 to 7:1 (v/w) are preferred.

An alternative consists in the addition of a base in an amount equal to or higher than the mole difference between racemic acid and resolution agent, in order to keep in solution the undesired isomer in the form of salt. Suitable bases are those giving salts soluble in the solvent used, for example low weight trialkylamines.

The mixture, whatever obtained, is heated to a temperature sufficient for a complete dissolution, i.e. at temperatures from 40° C. to the mixture's reflux temperature, then it is cooled slowly and preferably seeded with some previously prepared diastereomeric salt. The diastereomeric salt is left to crystallize, then is cooled at a temperature and for a time so as to obtain the maximum yield in so far as the optical purity of the diastereomeric salt allows. Such a temperature can range from 40° C. to −10° C., whereas the cooling time can range from 30' to several hours. The resulting suspension is filtered, recovering the diastereomeric salt, whose optical purity can be improved by recrystallization.

For this purpose, the salt is suspended in the same solvent or solvent mixture as used for the resolution and heated to a clear solution. (For the solvent amounts and the temperatures, what stated above applies). The solution is then cooled, precipitating the purified diastereomeric salt.

Said salt is then decomposed by addition of alkali (for example NaOH or KOH) in a mixture of water and a water-immiscible solvent, thereby obtaining an aqueous solution of a Naproxene salt (for example sodium or potassium) and an organic solution of the resolution agent (which can be recovered and recycled).

The desired (+) form, i.e. Naproxene, is precipitated by addition of an organic or mineral acid to the solution of the above mentioned alkali salt.

From the precipitation mother liquors of the diastereomeric salt, using per se known procedures, the solvent, the resolution agent and the Naproxene undesired enantiomer are recovered, the latter being racemized with conventional techniques and recycled.

EXAMPLE 1
(−)-2-(4-Methoxybenzyl)amino-1-butanol 112.5 gr of p-anisaldehyde and 75 of R(−)-2-amino-1-butanol are dissolved in 500 ml of isopropanol. The mixture is stirred for 8 hours at 50° C. under hydrogen stream; then 3 g of 5% Pd/C are added, heating at 70° C. under a hydrogen stream for 24 hours.

The mixture is cooled at 20°–30° C., and the catalyst is filtered off. The solvent is evaporated under vacuum, the residue is taken up with 200 ml of chloroform (or toluene) and 100 ml of water, the phases are separated and the aqueous phase is re-extracted with some chloroform (or toluene).

From the combined organic extracts, by evaporation of the solvent, a residual oil is obtained which solidifies upon cooling.

160 g of the product with a 98% titre are obtained. Yield 89%. M.p.: 59.5°–61.5° C.; $\alpha_D$: (5% MeOH): −21°

Elementary analysis: for $C_{12}H_{19}NO_2$ (m.w.: 209.29):
 calculated: C=68.86%, N=6.69%
 found: C=68.91%, N=6.72%

EXAMPLE 2
(−)-2-(4-Methylbenzyl)amino-1-butanol

The process of example 1 is repeated, but using 100 g of p-tolylaldehyde instead of anisaldehyde. 145 g of the product with a 98% titre are obtained. Yield 89%. M.p.: 69°–70° C.; $\alpha_D$ (5% MeOH): −24.1°

Elementary analysis: for $C_{12}H_{19}NO$ (m.w.: 193.29):
 calculated: C=74.56%, N=7.25%
 found: C=74.60%, N=6.31%

EXAMPLE 3
(−)-2-(Benzyl)amino-1-butanol

The process of example 1 is repeated, but using 87 g of benzaldehyde instead of anisaldehyde. 145 g of the product with a 98% titre are obtained. Yield 89%. M.p.: 74°–75° C.; $\alpha_D$ (5% MeOH): −24°

Elementary analysis: for $C_{11}H_{17}NO$ (m.w.: 179.26):
 calculated: C=73.70, N=7.82%
 found: C=73.89%, N=7.85%

EXAMPLE 4
(−)-2-(4-Methoxybenzyl)amino-1-butanol

The process of example 1 is repeated, but using n-butanol instead of isopropanol. 163 g of the product with a 98% titre are obtained. Yield 87.5%. M.p.: 60°–61° C.; $\alpha_D$ (5% MeOH): −20.9°

Elementary analysis: for $C_{12}H_{19}NO_2$ (m.w.: 209.29):
 calculated: C=68.86%, N=6.69%
 found: C=68.88%, N=6.74%

EXAMPLE 5
(−)-2-(2-Phenyl-propyl)amino-1-butanol 111 g of 2-phenylpropanal and 75 of R(−)-2-amino-1-butanol are dissolved in 500 ml of isopropanol, stirring for 8 hours at 50° C. under a hydrogen stream. 3 g of 5% Pd/C are added to the mixture, which is heated at 70° C. with a hydrogen stream for 24 hours, then cooled at 20°–30° C. and the catalyst is filtered off.

The solvent is evaporated under vacuum and the residue is taken up with 200 ml of chloroform (or toluene) and 100 ml of water, the phases are separated, the aqueous phase is re-extracted with some chloroform (or toluene) and the combined organic extracts are evaporated; the residual oil solidifies upon cooling.

158 g of the product with a 98% titre are obtained. Yield 89%. M.p.: 58.5°–60.5° C.; $\alpha_D$ (5% MeOH): −21.2°.

Elementary analysis: for $C_{12}H_{19}NO_2$ (m.w.: 207.32):
 calculated: C=75.31%, N=6.76%
 found: C=75.57%, N=6.79%

EXAMPLE 6
(+)-6-Methoxy-α-methyl-2-naphthaleneacetic acid (−)-2-(4-methoxybenzyl)amino-1-butanol salt 46 g of racemic acid are dissolved in a mixture of 180 ml of acetone and 40 ml of water at 50° C. 27 g of (−)-2-(4-methoxybenzyl)amino-1-butanol are added quickly and the mixture is heated to reflux, then cooled to 50°. 0.5 g of the title salt (obtained in a previous cycle) are added to the mixture, which is kept at 50° C. for 2 hours to crystallize the salt, then is cooled slowly to 20° C. and maintained for a further 2 hours at said temperature. The precipitated crystals are filtered off and washed with 30 ml of an acetone/water 82/18 mixture.

The product is poured into a mixture of 128 ml of acetone and 32 ml of water and the suspension is heated to reflux, then left to cool at room temperature and after that cooled at 0° C. for 2 hours. The precipitated crystals are filtered off and washed with 30 ml of an acetone/water 82/18 mixture. Yield: g 33 of pure title salt equivalent to 75% of the theoretical. M.p.: 150°–151° C.; $\alpha_D$ (5% MeOH/NaOH 1N 75/25): −15.5°. Titre: 99%.

Elementary analysis: for $C_{26}H_{33}NO_5$ (m.w.: 439.55):
 calculated: C=71.04%, N=3.19%
 found: C=71.38%, N=3.22%

From the mother liquors which still contain the undesired enantiomer partly salified with the resolution agent, the racemic acid and part of the resolution agent are recovered, as it will be described in examples 14 and 15. From the diastereomeric salt, Naproxene is recovered as described in example 13 and the remaining resolution agent is recovered as reported in example 15.

EXAMPLE 7
(+)-6-Methoxy-α-methyl-2-naphthaleneacetic Acid (−)-2-(4-methoxybenzyl)amino-1-butanol Salt 46 g of racemic acid are dissolved in a mixture of 180 ml of methyl ethyl ketone and 40 ml of water at 50° C. 27 g of (−)-2-(4-methoxybenzyl)amino-1-butanol are added quickly and the mixture is refluxed. After that, the procedure of the example 6 is followed, replacing acetone with methyl ethyl ketone.

Yield: 29 g of pure title salt, equivalent to 66% of the theoretical. M.p.: 150°–151° C.; $\alpha_D$ (5% MeOH/1N NaOH 75/25): −15.3°. Titre: 99%.

Elementary analysis: for $C_{26}H_{33}NO_5$ (m.w.: 439.55):
    calculated: C=71.04%, N=3.19%
    found: C=71.38%, N=3.22%

From the mother liquors which still contain the undesired enantiomer partly salified with the resolution agent, the racemic acid and part of the resolution agent are recovered, as it will be described in examples 14 and 15. From the diastereomeric salt, Naproxene is recovered as described in example 13 and the remaining resolution agent is recovered as reported in example 15.

EXAMPLE 8
(+)-6-Methoxy-α-methyl-2-naphthaleneacetic Acid (−)-2-(4-methoxybenzyl)amino-1-butanol Salt 46 g of racemic acid are dissolved in a mixture of 200 ml of acetone and 20 ml of water at 50° C. 27 g of (−)-2-(4-methoxybenzyl)amino-1-butanol are added quickly and the mixture is refluxed. After that, the procedure of the example 6 is followed, replacing the acetone/water 82/18 mixture with a mixture of the same solvents in a 91/9 ratio.

Yield: 33 g of pure (+)-6-methoxy-α-methyl-2-naphthaleneacetic acid (−)-2-(4-methoxybenzyl)amino-1-butanol salt, equivalent to 75% of the theoretical. M.p. : 149°–151° C.; $\alpha_D$ (5% MeOH/1N NaOH 75/25): −14.9°. Titre: 99%

Elementary analysis: for $C_{26}H_{33}NO_5$ (m.w.: 439.55):
    calculated: C=71.04%, N=3.19%
    found: C=71.38%, N=3.22%

From the mother liquors which still contain the undesired enantiomer partly salified with the resolution agent, the racemic acid and part of the resolution agent are recovered, as it will be described in examples 14 and 15. From the diastereomeric salt, Naproxene is recovered as described in example 13 and the remaining resolution agent is recovered as reported in example 15.

EXAMPLE 9
(+)-6-Methoxy-α-methyl-2-naphthaleneacetic Acid (−)-2-(4-methylbenzyl)amino-1-butanol Salt 46 g of racemic acid are dissolved in a mixture of 200 ml of acetone and 20 ml of water at 50° C. 25 g of (−)-2-(4-methylbenzyl)amino-1-butanol are added quickly and the mixture is refluxed. After that, the procedure of the example 6 is followed. Yield: 17 g of pure (+)-6-methoxy-α-methyl-2-naphthaleneacetic acid (−)-2-(4-methylbenzyl)amino-1-butanol salt, equivalent to 40% of the theoretical. M.p.: 143°–143.5°; $\alpha_D$ (5% MeOH/1N NaOH 75/25): −15.8°. Titre: 99%.

Elementary analysis: for $C_{26}H_{33}NO_4$ (m.w.: 423.55.):
    calculated: C=73.73%, N=3.31%
    found: C=73.78%, N=3.38%

From the mother liquors which still contain the undesired enantiomer partly salified with the resolution agent, the racemic acid and part of the resolution agent are recovered, as it will be described in examples 14 and 15. From the diastereomeric salt, Naproxene is recovered as described in example 13 and the remaining resolution agent is recovered as reported in example 15.

EXAMPLE 10
(+)-6-Methoxy-α-methyl-2-naphthaleneacetic Acid (−)-2-(4-methylbenzyl)amino-1-butanol Salt 46 g of racemic acid are dissolved in a mixture of 250 ml of acetone at 50° C. 25 g of (−)-2-(4-methylbenzyl)amino-1-butanol are added quickly and the mixture is refluxed. After that, the procedure of the example 6 is followed.

Yield: 17 g of the title compound, equivalent to 40% of the theoretical. M.p.: 143°–144° C.; $\alpha_D$ (5% MeOH/1N NaOH 75/25): −15.9° Titre: 99%.

Elementary analysis: for $C_{26}H_{33}NO_4$ (m.w.: 423.55):
    calculated: C=73.73%, N=3.31%
    found: C=73.75%, N=3.34%

From the mother liquors which still contain the undesired enantiomer partly salified with the resolution agent, the racemic acid and part of the resolution agent are recovered, as it will be described in examples 14 and 15. From the diastereomeric salt, Naproxene is recovered as described in example 13 and the remaining resolution agent is recovered as reported in example 15.

EXAMPLE 11
(+)-6-methoxy-α-methyl-2-naphthaleneacetic Acid (−)-2-(4-methylbenzyl)amino-1-butanol Salt 46 g of racemic acid are dissolved in a mixture of 105 ml of toluene and 45 ml of methanol at 50°C. 34 g of (−)-2-(4-methylbenzyl)amino-1-butanol and 18 g of triethylamine are added quickly. The mixture is refluxed, cooled to 35° C., added with 0.5 g of diastereomeric salt, left to crystallize and cooled at 20° C. for 2 hours. The precipitate is filtered and washed with 50 ml of a toluene/methanol 70/30 mixture.

15 g of the title compound are obtained, equivalent to 35% of the theoretical. M.p.: 141°–143° C.; $\alpha_D$ (5% MeOH/1N NaOH 75/25): −14.9°. Titre: 98.2%.

Elementary analysis: for $C_{26}H_{33}NO_4$ (m.w.: 423.55):
    calculated: C=73.73%, N=3.31%
    found: C=73.80%, N=3.39%

EXAMPLE 12
(+)-6-methoxy-α-methyl-2-naphthaleneacetic Acid (−)-2-(benzyl)amino-1-butanol Salt 46 g of racemic acid are dissolved in a mixture of 180 ml of acetone and 40 ml of water at 50° C. 23 g of (−)-2-(benzyl)amino-1-butanol are added quickly and the mixture is refluxed. After that, the procedure of the example 6 is followed.

Yield: 9.5 g of pure title salt, equivalent to 23% of the theoretical. M.p.: 127°–128° C.; $\alpha_D$ (5% MeOH/1N NaOH 75/25): −16°. Titre: 98.9%.

Elementary analysis: for $C_{25}H_{31}NO_4$ (m.w.: 409.53):
    calculated: C=73.32%, N=3.42%
    found: C=73.51%, N=3.55%

From the mother liquors which still contain the undesired enantiomer partly salified with the resolution agent, the racemic acid and part of the resolution agent are recovered, as it will be described in examples 14 and 15. From the diastereomeric salt, Naproxene is recovered as described in example 13 and the remaining resolution agent is recovered as reported in example 15.

EXAMPLE 13
(+)-6-Methoxy-α-methyl-2-naphthaleneacetic Acid (Naproxene)

The diastereomeric salt obtained in example 6 is poured into 100 ml of water and 100 ml of toluene (or chloroform). About 8–9 ml of 30% NaOH are dropped slowly therein until pH 12.5–13.0, at 20° C. The phases are separated: the organic phase contains the resolution agent (which is recovered as described in example 14), the aqueous one contains the (+)-6-methoxy-α-methyl-2-naphthaleneacetic acid sodium salt.

The aqueous phase is filtered through celite and heated at 80° C. Naproxene precipitates upon slow addition of acetic acid until pH 4–4.5 (alternatively, a diluted mineral acid can be added, such as 30% hydrochloric acid or 50% sulfuric acid). The resulting suspension is cooled to 20° C. and the product is separated by filtration and washed thoroughly with water, then dried in oven at 60° C.

17 g of (+)-6-methoxy-α-methyl-2-naphthaleneacetic acid (Naproxene) are obtained, equivalent to 98% of the theoretical based on the diastereomeric salt. M.p.: 156°–157° C.; $\alpha_D$=65.6°. Titre: 99.7%.

Elementary analysis: for $C_{14}H_{14}O_3$ (m.w.: 230.26):

calculated: C=73.03%, N=6.08% found: C=73.11%, N=6.13%

EXAMPLE 14

Recovery of (±)-6-methoxy-α-methyl-2-naphthaleneacetic Acid

The mother liquors of the diastereomeric salt and from its purification of example 6 are combined and distilled under atmospheric pressure to recovery acetone. The residue is added with 100 ml of water and 100 ml of toluene (or chloroform). After that, about 16 ml of 30% NaOH are dropped slowly until pH 12.5–13 and the phases are separated: the organic phase contains the resolution agent which will be recovered as described in example 15; the aqueous phase is added with 12 g of solid NaOH and refluxed for 10 hours. Then it is cooled, diluted with 300 ml of water, heated to 80° C. and acetic acid (or a diluted mineral acid) is added slowly until pH 4–4.5. The resulting suspension is cooled at 20° C. and the precipitate is separated by filtration, washed thoroughly with water and dried in oven at 60° C.

26.5 g of (±)-6-methoxy-α-methyl-2-naphthaleneacetic acid are recovered. M.p.: 156°–158° C.; $\alpha_D$=0°. Titre= 98.7%.

The total yield of the optical resolution is therefore 17 g of Naproxene+26.5 g of racemic acid=43.5, equivalent to 94.5% of the starting racemic acid (example 6).

EXAMPLE 15

Recovery of the Resolution Agent

The extraction solvent from the recovery of Naproxene (example 13) and from the recovery of the racemic acid (example 14) is collected and distilled under reduced pressure. The distillate (toluene or chloroform) can be recycled with no further treatments. The distillation residue consists of the resolution agent. 24.6 g of the product are obtained, with a 98% titre.

The recovery yield (based on the amount used in example 6) is 91%.

In order to evaluate the optical purity of the diastereomeric salts obtained in the different examples, salts of a sample of pure. Naproxene ($\alpha_D$:+67°) with the resolution agents were prepared, with the following results:

Naproxene (−)-2-(benzyl)amino-1-butanol salt=−16.1°

Naproxene (−)-2-(4-methylbenzyl)amino-1-butanol salt=− 16°

Naproxene (−)-2-(4-methoxybenzyl)amino-1-butanol salt=− 15.61°

We claim:

1. A process for the resolution of (±)-6-methoxy-α-methyl-2-naphthaleneacetic acid into its enantiomers which comprises reacting said acid with (−)-2-(4-methoxybenzyl) amino-1-butanol as a resolution agent in a suitable solvent at a temperature of from 40° C. to the reflux temperature of the resultant solution; cooling the resultant solution to precipitate the salt of said acid and said resolution agent; separating the precipitated salt; and treating the remaining solution to recover residual acid and resolution agent.

2. A process according to claim 1 in which said acid and resolution agent are present in a mol ratio of 0.5–1.0.

3. A process according to claim 2 in which the solvent is selected from the group consisting of acetone, methylethyl ketone, ethyl acetate, acetone/water, toluene/methanol and toluene/ethanol, and the solvent/acid ratio is 2:1 to 20:1 vol/wt.

* * * * *